(12) United States Patent
Tang et al.

(10) Patent No.: US 10,835,484 B2
(45) Date of Patent: Nov. 17, 2020

(54) ORAL CARE COMPOSITIONS INCLUDING PLANT-BASED ABRASIVES AND METHODS FOR THE SAME

(71) Applicant: Colgate-Palmolive Company, New York, NY (US)

(72) Inventors: Saide Tang, Princeton, NJ (US); Lin Fei, Kendall Park, NJ (US); Suman Chopra, Monroe, NJ (US); Abhishek Agrawal, Kendall Park, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 16/232,964

(22) Filed: Dec. 26, 2018

(65) Prior Publication Data

US 2020/0206125 A1    Jul. 2, 2020

(51) Int. Cl.
*A61K 8/9789* (2017.01)
*A61Q 11/00* (2006.01)
*A61K 8/25* (2006.01)

(52) U.S. Cl.
CPC ........... *A61K 8/9789* (2017.08); *A61K 8/25* (2013.01); *A61Q 11/00* (2013.01); *A61K 2800/28* (2013.01)

(58) Field of Classification Search
None
See application file for complete search history.

(56) References Cited

U.S. PATENT DOCUMENTS 5,830,445 A    11/1998   Bouillon et al.
6,126,444 A    10/2000   Horiguchi

FOREIGN PATENT DOCUMENTS

| CN | 104248571 A | * | 12/2014 |
| KR | 20100034929 A | | 4/2010 |
| KR | 20120011351 | * | 2/2012 |
| KR | 20120011351 A | * | 2/2012 |
| KR | 20120011351 A | | 2/2012 |

OTHER PUBLICATIONS

Lincoln Park Smiles (https://www.lincolnparksmiles.com/tooth-whitening-tips-the-natural-way/) (Year: 2013).*
Amorepacific, 2011, "Toothpaste with Walnut Powder," Database Mintel GNPD AN: 1482564.
KR20100034929A, Amorepacific Corp, "Oral Composition for Effective Plaque Care," Apr. 2, 2010, English language machine translation of abstract, Espacenet, date obtained: Dec. 31, 2019, 1 Page <https://worldwide.espacenet.com/patent/search/family/042212941/publication/KR20100034929A?q=KR20100034929A>.
Nature's Answer, 2017, "Natural Brightening Toothpaste with CoQ10 & Folic Acid," Database GNPD AN: 5291817.
Swanson Health Products, 2012, "Peppermint Flavored Whitening Toothpaste," Database GNPD AN: 1944940.

* cited by examiner

*Primary Examiner* — Celeste A Roney

(57) ABSTRACT

An oral care composition and methods for whitening teeth are disclosed herein. The whitening composition may include an orally acceptable vehicle and one or more abrasives. The one or more abrasives may include at least one plant-based abrasive. The method for whitening teeth may include contacting the oral care composition with surfaces of the teeth at least twice a day for at least nine days.

9 Claims, No Drawings

ORAL CARE COMPOSITIONS INCLUDING PLANT-BASED ABRASIVES AND METHODS FOR THE SAME

BACKGROUND

Conventional oral care products (e.g., dentifrices) and compositions thereof may often incorporate abrasives, such as abrasive silicas, to clean plaque and stains from surfaces of teeth. In addition to removing plaque and stains, the abrasives may also be capable of polishing the teeth to thereby increase the gloss and shine thereof. While conventional oral care products incorporating abrasives have proven to be effective for removing plaque and stains, and for increasing gloss and shine, increased concerns of consumers have resulted in increased interest in more natural and/or organic oral care products.

What is needed, then, are improved oral care products including natural abrasives, and methods for the same.

BRIEF SUMMARY

This summary is intended merely to introduce a simplified summary of some aspects of one or more implementations of the present disclosure. Further areas of applicability of the present disclosure will become apparent from the detailed description provided hereinafter. This summary is not an extensive overview, nor is it intended to identify key or critical elements of the present teachings, nor to delineate the scope of the disclosure. Rather, its purpose is merely to present one or more concepts in simplified form as a prelude to the detailed description below.

The foregoing and/or other aspects and utilities embodied in the present disclosure may be achieved by providing an oral care composition including an orally acceptable vehicle and one or more abrasives. The one or more abrasives may include at least one plant-based abrasive.

In at least one implementation, the at least one plant-based abrasive may include one or more of a tree bark abrasive, a tree branch abrasive, a tree trunk abrasive, or combinations thereof.

In at least one implementation, the at least one plant-based abrasive may include one or more of a walnut bark abrasive, a walnut trunk abrasive, a walnut branch abrasive, or combinations thereof.

In at least one implementation, the one or more abrasives may further include a silica abrasive.

In at least one implementation, the one or more abrasives may be present in the oral care composition in an amount of from about 10 weight % to about 30 weight %, based on a total weight of the oral care composition.

In at least one implementation, the at least one plant-based abrasive is present in an amount of from about 5 weight % to about 15 weight %, based on a total weight of the oral care composition.

In at least one implementation, the silica abrasive is present in an amount of from about 5 weight % to about 15 weight %, based on a total weight of the oral care composition.

In at least one implementation, the one or more abrasives may include only the at least one plant-based abrasive.

In at least one implementation, the at least one plant-based abrasives may only include or consist of walnut tree branch powder.

In at least one implementation, the at least one plant-based abrasives may include only walnut tree trunk powder.

In at least one implementation, the oral care composition is a whitening toothpaste.

The foregoing and/or other aspects and utilities embodied in the present disclosure may be achieved by providing a method for whitening teeth of a subject, comprising contacting any one or more of the oral care composition disclosed herein with a surface of the teeth of the subject in need thereof.

In at least one implementation, contacting the oral care composition with the surface of the teeth may include directly applying the oral care composition to the surface of the teeth with a delivery device, optionally, the delivery device is a toothbrush.

In at least one implementation, the oral care composition is contacted with the surface of the teeth for at least 2 minutes.

In at least one implementation, the method may include contacting the oral care composition with the surface of the teeth at least twice a day for at least 7 days, optionally, at least 9 days, further optionally, at least 14 days.

Further areas of applicability of the present disclosure will become apparent from the detailed description provided hereinafter. It should be understood that the detailed description and specific examples, while indicating some typical aspects of the disclosure, are intended for purposes of illustration only and are not intended to limit the scope of the disclosure.

DETAILED DESCRIPTION

The following description of various typical aspect(s) is merely exemplary in nature and is in no way intended to limit the disclosure, its application, or uses.

As used throughout this disclosure, ranges are used as shorthand for describing each and every value that is within the range. It should be appreciated and understood that the description in a range format is merely for convenience and brevity, and should not be construed as an inflexible limitation on the scope of any embodiments or implementations disclosed herein. Accordingly, the disclosed range should be construed to have specifically disclosed all the possible subranges as well as individual numerical values within that range. As such, any value within the range may be selected as the terminus of the range. For example, description of a range such as from 1 to 5 should be considered to have specifically disclosed subranges such as from 1.5 to 3, from 1 to 4.5, from 2 to 5, from 3.1 to 5, etc., as well as individual numbers within that range, for example, 1, 2, 3, 3.2, 4, 5, etc. This applies regardless of the breadth of the range.

Unless otherwise specified, all percentages and amounts expressed herein and elsewhere in the specification should be understood to refer to percentages by weight. The amounts given are based on the active weight of the material.

Additionally, all numerical values are "about" or "approximately" the indicated value, and take into account experimental error and variations that would be expected by a person having ordinary skill in the art. It should be appreciated that all numerical values and ranges disclosed herein are approximate values and ranges, whether "about" is used in conjunction therewith. It should also be appreciated that the term "about," as used herein, in conjunction with a numeral refers to a value that may be ±0.01% (inclusive), ±0.1% (inclusive), ±0.5% (inclusive), ±1% (inclusive) of that numeral, ±2% (inclusive) of that numeral, ±3% (inclusive) of that numeral, ±5% (inclusive) of that numeral, ±10% (inclusive) of that numeral, or ±15% (inclusive) of that numeral. It should further be appreciated that when a numerical range is disclosed herein, any numerical value falling within the range is also specifically disclosed.

As used herein, "free" or "substantially free" of a material may refer to a composition, component, or phase where the material is present in an amount of less than 10.0 weight %, less than 5.0 weight %, less than 3.0 weight %, less than 1.0 weight %, less than 0.1 weight %, less than 0.05 weight %, less than 0.01 weight %, less than 0.005 weight %, or less than 0.0001 weight % based on a total weight of the composition, component, or phase.

All references cited herein are hereby incorporated by reference in their entireties. In the event of a conflict in a definition in the present disclosure and that of a cited reference, the present disclosure controls.

The present inventors have surprisingly and unexpectedly discovered that whitening compositions including one or more of tree bark abrasives, tree branch abrasives, tree trunk abrasives, or the like, or mixtures or combinations thereof exhibit relatively greater whitening efficacy than conventional whitening compositions including conventional abrasives. Particularly, it was surprisingly and unexpectedly discovered that incorporating tree branch powder, namely walnut branch powder, and tree trunk powder, namely walnut trunk powder, into whitening compositions provided relatively greater whitening efficacy as compared to conventional abrasives (e.g., abrasive silica) alone. The whitening efficacy is more pronounced after at least one week or at least about 9 days of brushing twice a day.

Compositions

Compositions disclosed herein may be or include an oral care product, an oral care composition, and/or a whitening composition thereof. For example, the composition may be an oral care product including a whitening composition, or the whitening composition thereof. The oral care product or the whitening composition thereof may include a carrier or an orally acceptable vehicle and one or more abrasives.

In at least one implementation, the oral care product or the whitening composition thereof prior to use may contain water in an amount of greater than about 10 weight %, greater than about 15 weight %, greater than about 20 weight %, or greater than about 25 weight %, based on a total weight of the oral care composition. In another implementation, the oral care product or the whitening composition thereof may be anhydrous or non-aqueous prior to use. For example, the oral care product or the whitening composition thereof may be free of water, substantially free of water. As used herein, "free of water" or "substantially free of water" may refer to a composition that contains water in an amount of less than 10 weight %, less than 8 weight %, less than 5 weight %, less than 3 weight %, less than 1 weight %, less than 0.1 weight %, less than 0.05 weight %, less than 0.01 weight %, less than 0.005 weight %, or less than 0.0001 weight %, based on a total weight of the oral care product or the whitening composition thereof. In yet another implementation, the oral care product or the whitening composition thereof prior to use may have a "low water content". As used herein, "low water content" may refer to a composition that contains water in an amount greater than about 5 weight % or greater than about 10 weight %, and less than about 20 weight %, less than about 15 weight %, or less than about 10 weight %, based on a total weight of the oral care product or the whitening composition thereof.

Abrasives

The oral care product or the whitening composition thereof may include one or more abrasives. As used herein, the term "abrasive" may refer to materials commonly referred to as "polishing agents." The one or more abrasives may be mixed, combined, dispersed, suspended, or otherwise contacted with the orally acceptable vehicle. In at least one implementation, the oral care product or the whitening composition thereof includes a single abrasive. In another implementation, the oral care product or the whitening composition thereof includes a mixture or combination of at least two abrasives. In a preferred implementation, the abrasives include at least one plant-based abrasive, such as walnut trunk, walnut branch, or combinations thereof. In another implementation, the abrasives may include at least one plant-based abrasive, such as tree bark abrasives, and another conventional abrasive, such as abrasive silica.

Illustrative abrasives may be or include, but are not limited to, plant-based abrasives. Any one or more portions or parts of the plant may be utilized as the abrasive. For example, the plant-based abrasives may be derived from roots, flowers, buds, stems, shoots, leaves, bulbs, grains, nuts, seeds, beans, fruits, fruit skins, barks, trunks, branches, stalks, shafts, or the like, or any combination thereof. Illustrative plant-based abrasives may be or include, but are not limited to, tree bark abrasives, tree branch abrasives, tree trunk abrasives, walnut bark abrasives, walnut trunk abrasives, walnut branch abrasives, walnut shell abrasives, or the like, or any mixture or combination thereof. The type of walnut tree is not limited. Branches of the walnut tree may include any one or more portions of the tree branches, including the bark, the shaft, or the like, or any combination thereof. The plant-based abrasives may be used directly or dried. In at least one implementation, any one or more of the plant-based abrasives may be associated with an extract of the plant. For example, any one or more of the plant-based abrasives may include walnut bark extract. In another implementation, any one or more of the plant-based abrasives may not include any extract of the plant.

Illustrative conventional abrasives may be or include, but are not limited to, metaphosphate compounds, phosphate salts (e.g., insoluble phosphate salts), such as sodium metaphosphate, potassium metaphosphate, calcium pyrophosphate, magnesium orthophosphate, trimagnesium orthophosphate, tricalcium phosphate, dicalcium phosphate dihydrate, anhydrous dicalcium phosphate, calcium carbonate, magnesium carbonate, hydrated alumina, abrasive silicas, silica, silicates, zirconium silicate, aluminum silicate, calcined aluminum silicate, polymethyl methacrylate, or the like, or mixtures or combinations thereof.

The one or more abrasives may be provided in any suitable form. For example, the one or more abrasives may be provided as a powder, pellets, particles, a suspension, chips, or the like, or any combination thereof. In a preferred implementation, the abrasives are in the form of a powder. For example, the plant-based abrasives may include walnut trunk powder, walnut branch powder, or the like, or mixtures thereof. As discussed above, the oral care product or the oral care composition thereof may include at least one plant-based abrasive and another conventional abrasive. For example, the oral care product or the oral care composition thereof may include at least one plant-based abrasive, such as walnut trunk powder, walnut branch powder, walnut bark powder, or combinations thereof, and a conventional abrasive, such as silica.

The one or more of the abrasives in the abrasive system may have a pellicle cleaning ratio (PCR) greater than or equal to 80, greater than or equal to 82, greater than or equal to 84, greater than or equal to 86, greater than or equal to 88, greater than or equal to 90, greater than or equal to 92, greater than or equal to 94, greater than or equal to 96, greater than or equal to 98, greater than or equal to 100, greater than or equal to 102, greater than or equal to 104, greater than or equal to 106, greater than or equal to 108, greater than or equal to 110, greater than or equal to 112, or greater.

The amount or concentration of the one or more abrasives present in the oral care product or the oral care composition thereof may vary widely. In at least one implementation, the amount or concentration of the abrasives may be from greater than 0 weight % to about 40 weight %, based on a total weight of the oral care product or the composition thereof. For example, the amount of the abrasives present in the oral care composition may be from greater than 0 weight %, about 2 weight %, about 4 weight %, about 6 weight %, about 8 weight %, about 10 weight %, about 12 weight %, about 14 weight %, about 16 weight %, about 18 weight %, or about 19 weight % to about 21 weight %, about 22 weight %, about 24 weight %, about 26 weight %, about 28 weight %, about 30 weight %, about 32 weight %, about 34 weight %, about 36 weight %, about 38 weight %, or about 40 weight %. In another example, the amount of the abrasives present in the oral care composition may be from greater than 0 weight % to about 40 weight %, about 2 weight % to about 38 weight %, about 4 weight % to about 36 weight %, about 6 weight % to about 34 weight %, about 8 weight % to about 32 weight %, about 10 weight % to about 30 weight %, about 12 weight % to about 28 weight %, about 14 weight % to about 26 weight %, about 16 weight % to about 24 weight %, about 18 weight % to about 22 weight %, or about 19 weight % to about 21 weight %. In a preferred implementation, the amount of the abrasives present in the oral care composition may be from about 18 weight % to about 22 weight %, preferably about 19 weight % to about 21 weight %, or more preferably about 20 weight %, based on a total weight of the oral care product or the composition thereof.

Orally Acceptable Vehicle or Liquid Carrier

The whitening composition may form at least a portion of or be used in one or more oral care products or oral care compositions. The whitening composition may be mixed, dispersed, dissolved, combined, or otherwise contacted with an orally acceptable vehicle or carrier to form the oral care product (e.g., whitening toothpaste) or oral care compositions. Illustrative oral care products may include, but are not limited to, a mouthwash, a toothpaste (dentifrice), a prophylactic paste, a tooth powder, a tooth polish, a tooth gel (e.g., a whitening gel), a chewing gum, a lozenge, a whitening strip, a paint-on gel, varnish, veneer, tube, syringe, dental tray including a gel or paste, a gel or paste coated on an application support such as dental floss or a toothbrush (e.g., a manual, electric, sound, a combination thereof or ultrasound toothbrush), or any combination thereof. In a preferred implementation, the whitening composition may form at least a portion of or be used in a toothpaste, such as a whitening toothpaste.

In at least one implementation, the orally acceptable vehicle may include one or more humectants. Illustrative humectants may be or include, but are not limited to, glycerin, propylene glycol, sorbitol, polyethylene glycol, or the like, or mixtures or combinations thereof. In a preferred implementation, the orally acceptable vehicle may be or include, but is not limited to, sorbitol. The one or more humectants may be present in an amount of from 5 weight % to about 60 weight %, based on a total weight of the oral care product or the whitening composition thereof. For example, the one or more humectants may be present in an amount of from about 5 weight %, about 10 weight %, about 15 weight %, or about 20 weight % to about 25 weight %, about 30 weight %, about 35 weight %, about 40 weight %, about 45 weight %, about 50 weight %, about 55 weight %, or about 60 weight %, based on a total weight of the oral care product or the whitening composition thereof. In another example, the one or more humectants may be present in an amount of from about 5 weight % to about 60 weight %, about 10 weight % to about 55 weight %, about 15 weight % to about 50 weight %, about 20 weight % to about 25 weight %, about 20 weight % to about 40 weight %, about 20 weight % to about 35 weight %, about 20 weight % to about 30 weight %, or about 20 weight % to about 25 weight %, based on a total weight of the oral care product or the whitening composition thereof. In an exemplary implementation, the one or more humectants may be present in an amount of about 20 weight % to about 60 weight %, preferably about 30 weight % to about 50 weight %, more preferably about 40 weight % to about 50 weight %, or about 45 weight %, based on a total weight of the oral care product or the whitening composition thereof.

The orally acceptable vehicle may include one or more poloxamers. The poloxamers may be a liquid or a paste. The poloxamer may have an average molecular weight of less than or equal to about 12,000 Dalton (Da), less than or equal to about 11,000 Da, less than or equal to about 10,000 Da, less than or equal to about 9,000 Da, less than or equal to about 8,000 Da, less than or equal to about 7,000 Da, or less than or equal to about 6,000 Da. Illustrative poloxamers may be or include, but are not limited to, one or more of PLURONIC® L35 (poly(ethylene glycol)-block-poly(propylene glycol)-block-poly(ethylene glycol)), PLURONIC® L43, PLURONIC® L64, PLURONIC® L10, PLURONIC® L44, PLURONIC® L62, PLURONIC® 10R5, PLURONIC® 17R4, PLURONIC® L25R4, PLURONIC® P84, PLURONIC® P65, PLURONIC® P104, and PLURONIC® P105, or the like, or any mixture or combination thereof, each of which or commercially available from BASF Corp. of Florham Park, N.J. In a preferred implementation, the orally acceptable vehicle includes a poly(ethylene glycol)-block-poly(propylene glycol)-block-poly(ethylene glycol) polymer, such as PLURONIC® L35.

The orally acceptable vehicle may include a thickening system having one or more thickeners. The one or more thickeners may be any orally acceptable thickener or thickening agent configured to control the viscosity of the oral care product or the whitening composition thereof. Illustrative thickeners may be or include, but are not limited to, colloidal silica, fumed silica, thickening silica, polyvinylpyrrolidone (PVP), a cross-linked polyvinylpyrrolidone (PVP) polymer, cross-linked polyvinylpyrrolidone (PVP), or the like, or mixtures or combinations thereof. In at least one implementation, the thickening system includes a polyvinylpyrrolidone (PVP), cross-linked polyvinylpyrrolidone (PVP) polymer, or combinations thereof. The thickening system may also include POLYPLASDONE® XL 10F, which is commercially available from Ashland Inc. of Covington, Ky. Illustrative thickeners may also be or include, but are not limited to, carbomers (e.g., carboxyvinyl polymers), carrageenans (e.g., Irish moss, carrageenan, iota-carrageenan, etc.), high molecular weight polyethylene glycols (e.g., CARBOWAX®, which is commercially available from The Dow Chemical Company of Midland, Mich.), cellulosic polymers, hydroxyethylcellulose, carboxymethylcellulose, and salts thereof (e.g., CMC sodium), natural gums (e.g., karaya, xanthan, gum arabic, and tragacanth), colloidal magnesium aluminum silicate, or the like, or mixtures or combinations thereof.

In at least one implementation, the thickening system may include an organic polymer. Illustrative organic polymers may be or include, but are not limited to, hydrophilic polymers, such as carbomers, such as carboxymethylene polymers, such as acrylic acid polymers, and acrylic acid copolymers, carboxypolymethylene is a slightly acidic vinyl polymer with active carboxyl groups. In a typical embodiment, the thickening system includes a carboxypolymethylene, such as CARBOPOL® 974 and/or 980, which are commercially available from Noveon, Inc. of Cleveland, Ohio.

The amount or concentration of the thickening system and/or any one or more of the thickeners thereof present in the oral care product or the whitening composition thereof may vary widely. The amount of the thickening system and/or the thickeners thereof present in the oral care product or the whitening composition thereof may be from about 1 weight % to about 99 weight % based on the total weight of the oral care product or the whitening composition thereof. For example, the amount of the thickening system and/or the thickeners thereof present may be from about 1 weight %, about 2 weight %, about 3 weight %, about 4 weight %, about 5 weight %, about 6 weight %, about 7 weight %, about 8 weight %, about 9 weight %, about 10 weigh %, about 15 weight %, about 20 weight %, or about 21 weight % to about 22 weight %, about 23 weight %, about 24 weight %, about 25 weight %, about 26 weight %, about 27 weight %, about 28 weight %, about 29 weight %, about 30 weight %, or more, based on a total weight of the oral care product or the whitening composition thereof. In another example, the amount of the thickening system and/or the thickeners thereof present may be from about 1 weight % to about 10 weight %, about 2 weight % to about 9 weight %, about 3 weight % to about 8 weight %, about 4 weight % to about 7 weight %, or about 5 weight % to about 6 weight %, based on a total weight of the oral care product or the whitening composition thereof. In a typical implementation, the amount of the thickening system and/or the thickeners thereof present in the oral care product or the whitening composition thereof may be from about 10 weight % to about 20 weight %, more typically about 1.2 weight % to about 1.8 weight %, and more typically about 1.5 weight %.

Whitening Agent

The oral care product or the whitening composition thereof may include one or more whitening agents. The whitening agents may be or include, but are not limited to, hydrogen peroxide or one or more sources of hydrogen peroxide. For example, the whitening agents may be hydrogen peroxide and/or hydrogen peroxide releasing substances. The one or more sources of hydrogen peroxide may be or include any compound or material configured to release hydrogen peroxide. Preferably, the whitening agents include, but are not limited to, solid whitening agents and bound whitening agents which are substantially anhydrous oxygen generating compounds. Solid whitening agents may include, but are not limited to, peroxides and persulfates. Exemplary peroxide phases include hydroperoxides, hydrogen peroxide, peroxides of alkali and alkaline earth metals, organic peroxy compounds, peroxy acids, pharmaceutically-acceptable salts thereof, and mixtures thereof. Peroxides of alkali and alkaline earth metals include, but are not limited to, lithium peroxide, potassium peroxide, sodium peroxide, magnesium peroxide, calcium peroxide, barium peroxide, and mixtures thereof. Organic peroxy compounds include, but are not limited to, urea peroxide, glyceryl hydrogen peroxide, alkyl hydrogen peroxides, dialkyl peroxides, alkyl peroxy acids, peroxy esters, diacyl peroxides, benzoyl peroxide, and monoperoxyphthalate, and mixtures thereof. Peroxy acids and their salts include, but are not limited to, organic peroxy acids such as alkyl peroxy acids, and monoperoxyphthalate and mixtures thereof, as well as inorganic peroxy acid salts such as and perborate salts of alkali and alkaline earth metals such as lithium, potassium, sodium, magnesium, calcium and barium, and mixtures thereof. Preferred solid peroxides are sodium perborate, urea peroxide, and mixtures thereof. The whitening agents may be preferably bound. For example, peroxide may be bound to a polymer such as PVP (poly(N-vinylpyrrolidone). Suitable PVP complexes are disclosed, for example, in U.S. Pat. No. 5,122,370, the contents of which are incorporated herein by reference. In some implementations, it may be desirable to use any known whitening agent except sodium percarbonate and/or any of the percarbonate salts. The sources of hydrogen peroxide or whitening agents may also be or include, but are not limited to, PEROXYDONE™ XL 10 complex or POLYPLASDONE® XL 10F, which are commercially available from Ashland Inc. of Covington, Ky. In a typical implementation, the source of hydrogen peroxide includes a cross-linked PVP hydrogen peroxide complex. In at least one implementation, the oral care product or the whitening composition thereof may be free or substantially free of peroxide based whitening agents.

The amount or concentration of the source of hydrogen peroxide present in the oral care product or the whitening composition thereof may vary widely. In at least one example, the source of hydrogen peroxide may be present in an amount that provides a concentration of hydrogen peroxide of less than or equal to 4 weight %, less than or equal to 3.5 weight %, less than or equal to 3 weight %, less than or equal to 2.5 weight %, less than or equal to 2 weight %, or less than or equal to 1.5 weight %, based on a total weight of the oral care product or the composition thereof. In at least one implementation, the source of hydrogen peroxide may be present in an amount greater than or equal to 1 weight % and less than or equal to 30 weight %, based on a total weight of the oral care composition. For example, the source of hydrogen peroxide may be present in an amount of from about 1 weight %, about 3 weight %, about 5 weight %, about 7 weight %, about 9 weight %, about 11 weight %, about 13 weight %, or about 15 weight % to about 17 weight %, about 19 weight %, about 21 weight %, about 23 weight %, about 25 weight %, about 27 weight %, about 29 weight %, or about 30 weight %. In another example, the source of hydrogen peroxide may be present in an amount of from about 1 weight % to about 30 weight %, about 3 weight % to about 29 weight %, about 5 weight % to about 27 weight %, about 7 weight % to about 25 weight %, about 9 weight % to about 23 weight %, about 11 weight % to about 21 weight %, about 13 weight % to about 19 weight %, or about 15 weight % to about 17 weight %. In a preferred implementation, the source of hydrogen peroxide is a cross-linked PVP complexed with hydrogen peroxide, and is present in an amount of from about 8 weight % to about 14 weight %, preferably about 10 weight % to about 12 weight %, and more preferably about 11 weight %.

Surfactants or Surface Active Agents

The oral care product or the whitening composition thereof may include a surfactant or surfactant system including one or more surfactants. The surfactant may be configured to at least partially aid or facilitate the mixing or contact between one or more components of the oral care composition. For example, the surfactant may aid the mixing or facilitate contact between two or more phases (e.g., a hydrophobic component/phase and a hydrophilic component/phase) of the oral care product or the whitening composition thereof. The surfactants may be or include anionic, nonionic, cationic, amphoteric surfactants, or combinations thereof.

Illustrative surfactants may be or include, but are not limited to, water-soluble salts of $C_{8-20}$ alkyl sulfates, sulfonated monoglycerides of $C_{8-20}$ fatty acids, sarcosinates, taurates, sodium lauryl sulfate, sodium cocoyl monoglyceride sulfonate, sodium lauryl sarcosinate, sodium lauryl isoethionate, sodium laureth carboxylate, sodium dodecyl benzenesulfonate, cocoamidopropyl betaine, or the like, or combinations thereof. Illustrative surfactants or surface active agents may also be or include, but are not limited to, PLURONIC® L35, PLURONIC® L43, PLURONIC® L64, PLURONIC® L10, PLURONIC® L44, PLURONIC® L62, PLURONIC® 10R5, PLURONIC® 17R4, PLURONIC® L25R4, PLURONIC® P84, PLURONIC® P65, PLURONIC® P104, PLURONIC® P105, or the like, or combinations thereof, which are commercially available from BASF of Mount Olive, N.J. In a typical implementation, the surfactant is or includes a poly(ethylene glycol)-block-poly(propylene glycol)-block-poly(ethylene glycol) or PEG-PPG-PEG (PLURONIC® L-35).

The amount of the surfactants present in the oral care product or the whitening composition thereof may vary widely. In at least one implementation, the amount of one or more surfactants present in the oral care product or the whitening composition thereof may be greater than or equal to 0.0 weight % and less than or equal to 10.0 weight %, based on a total weight of the oral care product or the whitening composition thereof. For example, the amount of the surfactant present in the oral care product or the whitening composition thereof may be from about 0.0 weight %, about 1 weight %, about 2 weight %, about 3 weight %, about 4 weight %, or about 4.5 weight % to about 5.5 weight %, about 6 weight %, about 7 weight %, about 8 weight %, about 9 weight %, or about 10 weight %, based on a total weight of the oral care product or the whitening composition thereof. In another example, the amount of the surfactant present in the oral care product or the whitening composition thereof may be from about 0.0 weight % to about 10 weight %, about 1 weight % to about 9 weight %, about 2 weight % to about 8 weight %, about 3 weight % to about 7 weight %, about 4 weight % to about 6 weight %, or about 4.5 weight % to about 5.5 weight %, based on a total weight of the oral care product or the whitening composition thereof. In a preferred implementation, the amount of the surfactant present in the oral care product or the whitening composition thereof may be from about 1 weight % to about 6 weight %, more preferably about 2 weight % to about 3 weight %, more preferably about 2.5 weight %, based on a total weight of the oral care product or the whitening composition thereof.

Flavoring Agents

The oral care product or the whitening composition thereof may also include one or more flavoring agents. Illustrative flavoring agents may include, but are not limited to, essential oils and various flavoring aldehydes, esters, alcohols, or the like. The flavoring agents may also include, but are not limited to, sweeteners, sucralose, dextrose, polydextrose, sucrose, maltose, dextrin, dried invert sugar, mannose, xylose, ribose, fructose, levulose, galactose, corn syrup (including high fructose corn syrup and corn syrup solids), partially hydrolyzed starch, hydrogenated starch hydrolysate, sorbitol, mannitol, xylitol, maltitol, isomalt, aspartame, neotame, saccharin and salts thereof (e.g., sodium saccharin), dipeptide-based intense sweeteners, cyclamates, dihydrochalcones, or the like, or mixtures thereof. Examples of the essential oils include oils of spearmint, peppermint, wintergreen, *sassafras*, clove, sage, *eucalyptus*, marjoram, cinnamon, lemon, lime, grapefruit, and orange. In another example, the flavoring agents may include menthol, carvone, and anethole. In a preferred implementation, the flavoring agent includes peppermint and spearmint. In a more preferred implementation, the flavoring agent includes a Firmenich Newman Flavor.

The amount of any one or more of the flavoring agent in the oral care product or the whitening composition thereof may be less than 1.0 weight %, less than 0.9 weight %, less than 0.8 weight %, or less than 0.7 weight %. For example, the amount of the flavoring agent in the oral care product or the whitening composition thereof may be about 0.0 weight % to about 1.0 weight %, about 0.5 weight % to about 0.9 weight %, about 0.7 weight % to about 0.8 weight %. In a preferred implementation, the amount of the flavoring agent in the oral care product or the whitening composition thereof is about 0.01 weight % to about 0.4 weight %, preferably about 0.1 weight % to about 0.3 weight %, or about 0.2 weight %.

Additional Ingredients

It should be appreciated to one having ordinary skill in the art, that the oral care products and/or the whitening composition thereof may include other additional ingredients/components. For example, the oral care products and/or the whitening composition thereof may include pH modifying agents, anti-caries agents, desensitizing agents, viscosity modifiers, diluents, mouth feel agents, colorants, preservatives, or the like, or combinations or mixtures thereof. It should further be appreciated by one having ordinary skill in the art that while general attributes of each of the above categories of materials may differ, there may be some common attributes and any given material may serve multiple purposes within two or more of such categories of materials.

In at least one implementation, the additional ingredients/components may include one or more active materials configured to prevent and/or treat one or more conditions and/or disorders of the oral cavity. For example, the one or more active materials may be configured to prevent and/or treat one or more conditions and/or disorders of hard and/or soft tissue of the oral cavity. The active materials may also be configured to prevent and/or treat one or more physiological disorders and/or conditions, and/or provide a cosmetic benefit to the oral cavity.

In at least one implementation, the oral care products and/or the whitening composition thereof may be free or substantially free of fluoride (e.g., soluble fluoride salts). In another implementation, the oral care products and/or the whitening composition thereof may further include fluoride, such as one or more fluoride ion sources (e.g., soluble fluoride salts). A wide variety of fluoride ion-yielding materials may be employed as sources of soluble fluoride. Examples of suitable fluoride ion-yielding materials may be found in U.S. Pat. No. 3,535,421 to Briner et al., U.S. Pat. No. 4,885,155 to Parran, Jr. et al., and U.S. Pat. No. 3,678,154 to Widder et al., the disclosures of which are incorporated herein by reference. Illustrative fluoride ion sources include, but are not limited to, fluoride, stannous fluoride, sodium fluoride, potassium fluoride, sodium monofluorophosphate, fluorosilicate salts, such as sodium fluorosilicate and ammonium fluorosilicate, amine fluoride, ammonium fluoride, and combinations thereof. In a typical implementation, the fluoride ion source includes sodium fluoride. The amount of the fluoride ion source in the oral care composition may be greater than 0 weight % and less than 0.8 wt %, less than 0.7 wt %, less than 0.6 wt %, less than 0.5 wt %, or less than 0.4 wt %. The fluoride ion sources may be present in an amount sufficient to provide a total of about 100 to about 20,000 ppm, about 200 to about 5,000 ppm, or about 500 to about 2,500 ppm fluoride ions.

In at least one implementation, the oral care products and/or the whitening composition thereof may include an anticalculus agent. Generally, anticalculus agents may not be compatible with some whitening compositions, however, implementations of the present disclosure may incorporate anticalculus agents and the whitening composition into a single phase oral care product. Illustrative anticalculus agents may include, but are not limited to, phosphates and polyphosphates (e.g., pyrophosphates), polyaminopropane-sulfonic acid (AMPS), hexametaphosphate salts, zinc citrate trihydrate, polypeptides, polyolefin sulfonates, polyolefin phosphates, diphosphonates. In a typical implementation, the anticalculus agents includes tetrasodium pyrophosphate (TSPP), sodium tripolyphosphate (STPP), or a combination thereof.

The oral care products and/or the whitening composition thereof may optionally include one or more antimicrobial agents and/or one or more preservatives such as, methyl-isothiazolinone (MIT), sodium benzoate, potassium sorbate, benzyl alcohol, or the like, or combinations thereof. In another example, the oral care composition may include one or more antibacterial agents selected from halogenated diphenyl ether (e.g. triclosan), herbal extracts and essential oils (e.g., rosemary extract, tea extract, *magnolia* extract, thymol, menthol, eucalyptol, geraniol, carvacrol, citral, hinokitol, catechol, methyl salicylate, epigallocatechin gallate, epigallocatechin, gallic acid, miswak extract, sea-buckthorn extract), bisguanide antiseptics (e.g., chlorhexidine, alexidine or octenidine), quaternary ammonium compounds (e.g., cetylpyridinium chloride (CPC), benzalkonium chloride, tetradecylpyridinium chloride (TPC), N-tetradecyl-4-ethylpyridinium chloride (TDEPC)), phenolic antiseptics, hexetidine, octenidine, sanguinarine, povidone iodine, delmopinol, salifluor, other metal ions (e.g., stannous salts, copper salts, iron salts), sanguinarine, propolis and oxygenating agents (e.g., hydrogen peroxide, buffered sodium peroxyborate or peroxycarbonate), phthalic acid and its salts, monoperthalic acid and its salts and esters, ascorbyl stearate, oleoyl sarcosine, alkyl sulfate, dioctyl sulfosuccinate, salicylanilide, domiphen bromide, delmopinol, octapinol, and other piperidino derivatives, nicin preparations, chlorite salts; or mixtures of any of the foregoing. In a typical implementation, the antibacterial agent includes cetylpyridinium chloride (CPC). For example, all of the dual-phase mouthwash compositions disclosed herein may include CPC as an antibacterial agent.

The oral care products and/or the whitening composition thereof may include an antioxidant. Any orally acceptable antioxidant may be used, including, but not limited to, butylated hydroxyanisole (BHA), butylated hydroxytoluene (BHT), vitamin A, carotenoids, vitamin E, flavonoids, polyphenols, ascorbic acid, herbal antioxidants, chlorophyll, melatonin, or the like, or combinations or mixtures thereof.

The amount or concentration of any one or more of the additional ingredients/components present in the oral care product or the whitening composition thereof may vary widely. The amount of any one or more of any one or more of the additional ingredients/components present in the oral care product or the whitening composition thereof may be from about 1 weight % to about 99 weight %, based on the total weight of the oral care product or the whitening composition thereof. For example, the amount of any one or more of the additional ingredients/components present may be from about 1 weight %, about 2 weight %, about 3 weight %, about 4 weight %, about 5 weight %, about 6 weight %, about 7 weight %, about 8 weight %, about 9 weight %, about 10 weigh %, about 15 weight %, about 20 weight %, or about 21 weight % to about 22 weight %, about 23 weight %, about 24 weight %, about 25 weight %, about 26 weight %, about 27 weight %, about 28 weight %, about 29 weight %, about 30 weight %, or more, based on a total weight of the oral care product or the whitening composition thereof. In another example, the amount of any one or more of the additional ingredients/components present may be from about 1 weight % to about 99 weight %, about 3 weight % to about 90 weight %, about 14 weight % to about 80 weight %, about 15 weight % to about 80 weight %, about 16 weight % to about 70 weight %, about 17 weight % to about 60 weight %, about 18 weight % to about 50 weight %, about 19 weight % to about 40 weight %, or about 20 weight % to about 30 weight %. In a typical implementation, the amount of any one or more of the additional ingredients/components present in the oral care product or the whitening composition thereof may be from about 10 weight % to about 20 weight %, more typically about 1.2 weight % to about 1.8 weight %, and more typically about 1.5 weight %.

All ingredients for use in the compositions described herein should be orally acceptable. By "orally acceptable" as the term is used herein is meant an ingredient that is present in a composition as described in an amount and form that does not render the composition unsafe for use in the oral cavity.

Methods

The present disclosure also provides methods for whitening teeth in a human or animal subject with the oral care product and/or the whitening composition disclosed herein. As used herein "animal subject" may include higher order non-human mammals such as canines, felines, and horses. The method may include contacting the oral care product or the whitening composition thereof with surfaces of the oral cavity, such as surfaces of teeth.

In some implementations, contacting the surface of the teeth with the oral care product or the whitening composition thereof may include directly applying the oral care product or the whitening composition to the teeth using a delivery device, such as a pen, (e.g., a COLGATE® whitening pen or a COLGATE® ACTIS™ whitening pen, Colgate-Palmolive Company, New York. N.Y.), a liquid stick having an applicator, such as a felt tip, toothbrush, roller ball, non-woven pad, or the like.

The oral care product and/or the whitening composition thereof may be applied and/or contacted with the surfaces of the teeth at predetermined intervals. For example, a daily basis, at least once a day for multiple days, at least twice a day for multiple days, or alternatively every other day. In another example, the oral care product and/or the whitening composition thereof may be applied and/or contacted with the surfaces of the teeth at least once a day, at least twice a day, at least three times a day, or at least four times a day. The oral care product and/or the whitening composition thereof may be utilized for at least 1 day, at least 3 days, at least 6 days, at least 1 week, at least 9 days, at least 12 days, at least 2 weeks, at least 3 weeks, at least 4 weeks, at least 6 weeks, at least 8 weeks, or greater.

All ingredients for use in the compositions described herein should be orally acceptable. As used herein, "orally acceptable" may refer any ingredient that is present in a composition as described in an amount and form which does not render the composition unsafe for use in the oral cavity.

EXAMPLES

The examples and other implementations described herein are exemplary and not intended to be limiting in describing the full scope of compositions and methods of this disclosure. Equivalent changes, modifications and variations of specific implementations, materials, compositions and methods may be made within the scope of the present disclosure, with substantially similar results.

Example 1

The whitening efficacy of a control gel whitening composition (1) and two test whitening compositions (2) and (3) for whitening teeth was evaluated. Each of the control and test whitening compositions (2) and (3) was prepared by combining the components/ingredients according to Table 1. As indicated in Table 1, the control whitening composition (1) included about 20 weight % of an abrasive silica, the test whitening composition (2) included about 10 weight % of the abrasive silica and about 10 weight % of the walnut tree branch powder, and the test whitening composition (3) included about 10 weight % of the abrasive silica and about 10 weight % of the walnut tree trunk powder. The remaining components of the control and test whitening compositions (1)-(3) were the same.

TABLE 1

Composition of Control and Test Whitening Compositions (1)-(3)

| Ingredient | (1) | (2) | (3) |
|---|---|---|---|
| Abrasive Silica (wt %) | 20 | 10 | 10 |
| Walnut Tree Branch Powder (wt %) | — | 10 | — |
| Walnut Tree Trunk Powder (wt %) | — | — | 10 |
| Thickening Agent (wt %) | 5 | 5 | 5 |
| Water (wt %) | 21 | 21 | 21 |
| Colorants (wt %) | 0.5 | 0.5 | 0.5 |
| Orally Acceptable Surfactant (wt %) | 2.5 | 2.5 | 2.5 |
| Flavoring (wt %) | 1.6 | 1.6 | 1.6 |
| Excipient (wt %) | 49.4 | 49.4 | 49.4 |
| Total (wt %) | 100 | 100 | 100 |

To evaluate the whitening efficacy of the control and test whitening compositions (1)-(3), stained bovine teeth were obtained from Therametric Technologies, Inc. Specifically, a set of teeth, each set including four teeth, were used to evaluate each of the control and test whitening compositions (1)-(3). A slurry of each of the control and test whitening compositions (1)-(3) was prepared to mimic the toothpaste and water. To evaluate the whitening efficacy, each of the set of bovine teeth were treated with 28 whitening cycles. During each whitening cycle, a controlled amount of each of the slurries of the control and test whitening compositions (1)-(3) was added to a respective toothbrush and a control amount of pressure was applied to the toothbrush during brushing. Each of the set of teeth, including four stained bovine teeth, were brushed for about 2 minutes at the same rate. Each of the set of teeth were then rinsed with tap water to remove the slurry on the surface of the teeth. The whiteness of each of the teeth were measured at the baseline, after cycle 6, 12, 18, 24, and 28. It should be appreciated that the total of 28 whitening cycles mimic about 2 weeks of brushing twice a day.

The L*, a*, b* values were measured with a Hyperspectral Instrument (Model: MSV101L). The L*, a*, b* values were compared to baseline values measured before treatment to calculate the change in the whiteness of each of the bovine teeth. It should be appreciated that the whiteness index (W*) is a measure of overall color change relative to pure white, and is given by formula (1), and the change in whiteness index (ΔW*) is measured by formula (2). It should further be appreciated that the lower the whiteness index (ΔW*) the whiter the teeth. The change in whiteness index (ΔW*), or whitening efficacy, is summarized in Table 2.

$$W^* = ((L^*-100)^2 + (a^*)^2 + (b^*)^2)^{1/2} \quad (1)$$

$$\Delta W^* = W^*_{treated} - W^*_{baseline} \quad (2)$$

TABLE 2

Whitening Efficacy (ΔW*) of Control And Test Whitening Compositions (1)-(4)

| | | Number of Treatments | | | | | |
|---|---|---|---|---|---|---|---|
| | | 0 | 6 | 12 | 18 | 24 | 28 |
| (1) Silica | ΔW* | 0 | −1.07 | −1.47 | −2.29 | −2.90 | −3.37 |
| (2) 50/50 Silica + Branch | ΔW* | 0 | −1.30 | −1.82 | −2.37 | −3.49 | −3.76 |
| (3) 50/50 Silica + Trunk | ΔW* | 0 | −0.37 | −1.42 | −2.45 | −3.41 | −3.86 |

As illustrated in Table 2, the control whitening composition (1) and the test whitening composition (2) including walnut tree branch powder both exhibited similar whitening efficacy until about whitening cycle 18. As further illustrated in Table 2, the whitening efficacy of the control (1) and test (2) whitening compositions were relatively greater than the test whitening composition (3) including walnut tree trunk. It was surprisingly and unexpectedly discovered, however, that after 18 cycles of brushing, the test toothpaste whitening compositions (2) and (3) both outperformed the control whitening composition (1) in whitening efficacy. Accordingly, it was surprisingly and unexpectedly discovered that the walnut tree branch powder and the walnut tree trunk powder exhibited relatively greater whitening efficacy as compared to an abrasive silica alone after daily use for at least about 1 week or at least about 9 days.

The present disclosure has been described with reference to exemplary implementations. Although a limited number of implementations have been shown and described, it will be appreciated by those skilled in the art that changes may be made in these implementations without departing from the principles and spirit of the preceding detailed description. It is intended that the present disclosure be construed as including all such modifications and alterations insofar as they come within the scope of the appended claims or the equivalents thereof.

What is claimed is:

1. An oral care composition, comprising:
   an orally acceptable vehicle; and
   one or more abrasives comprising a silica abrasive and at least one plant-based abrasive, wherein the plant-based abrasive is selected from the group consisting of: a tree bark abrasive, a tree branch abrasive, a tree trunk abrasive, or combinations thereof;
   wherein the at least one plant-based abrasive is present in an amount of from about 5 weight % to about 15 weight %, based on a total weight of the oral care composition; and wherein the at least one plant-based abrasive comprises one or more of a walnut trunk abrasive, a walnut branch abrasive, or combinations thereof;

wherein the oral care composition contacts a surface of the teeth of a subject at least twice a day for at least 7 days.

2. The oral care composition of claim 1, wherein the one or more abrasives are present in the oral care composition in an amount of from about 10 weight % to about 30 weight %, based on a total weight of the oral care composition.

3. The oral care composition of claim 1, wherein the silica abrasive is present in an amount of from about 5 weight % to about 15 weight %, based on a total weight of the oral care composition.

4. The oral care composition of claim 1, wherein the one or more abrasives consist of the at least one plant-based abrasive.

5. The oral care composition of claim 4, wherein the at least one plant-based abrasives consist of walnut tree branch powder.

6. The oral care composition of claim 4, wherein the at least one plant-based abrasives consist of walnut tree trunk powder.

7. The oral care composition of claim 1, wherein the oral care composition is a whitening toothpaste.

8. The oral care composition of claim 1, wherein contacting the oral care composition with the surface of the teeth comprises directly applying the oral care composition to the surface of the teeth with a delivery device, optionally, the delivery device is a toothbrush.

9. The oral care composition of claim 8, wherein the oral care composition is contacted with the surface of the teeth for at least 2 minutes.

* * * * *